United States Patent
Moorthy et al.

(10) Patent No.: US 7,728,033 B2
(45) Date of Patent: Jun. 1, 2010

(54) MYCOPHENOLATE MOFETIL IN DIABETIC NEPHROPATHY

(75) Inventors: Sachidananda Moorthy, Karnataka (IN); Atignal Shankara Rao Arvind, Karnataka (IN)

(73) Assignee: Clinigene International Private Limited, Karnataka (IN)

( * ) Notice: Subject to any disclaimer, the term of this patent is extended or adjusted under 35 U.S.C. 154(b) by 865 days.

(21) Appl. No.: 10/983,465

(22) Filed: Nov. 8, 2004

(65) Prior Publication Data

US 2005/0250840 A1    Nov. 10, 2005

Related U.S. Application Data

(63) Continuation-in-part of application No. PCT/IN2004/000123, filed on May 5, 2004.

(30) Foreign Application Priority Data

May 5, 2003    (IN)    ..................... 377/03

(51) Int. Cl.
- *A01N 43/08* (2006.01)
- *A01N 43/00* (2006.01)
- *A61K 31/34* (2006.01)
- *A61K 31/33* (2006.01)
- *A61K 31/00* (2006.01)
- *C07D 307/00* (2006.01)

(52) U.S. Cl. .................. 514/468; 514/183; 514/210.21; 549/468

(58) Field of Classification Search ............ 514/210.21, 514/183, 468; 549/468
See application file for complete search history.

(56) References Cited

FOREIGN PATENT DOCUMENTS

| CA | 2 233 748 | 9/1999 |
|---|---|---|
| WO | WO 01/97809 | 12/2001 |
| WO | WO 2004/098587 | 11/2004 |

OTHER PUBLICATIONS

Hasslacher et al. "Natural Course of Diabetic Nephropathy". 2001, Chapter 2 from the book Diabetic Nephropathy, Edited by Christoph Hasslacher. John Wiley & Sons, Ltd. pp. 19-37.*
Richter et al. Proceedings of the National Academy of Science (PNAS). 1929, vol. 15, pp. 570-578.*
Ojogho et al. Pediatrics Transplantation. Apr. 2003, vol. 7, Issue 2, pp. 137-141.*
Lewis et al. New England Journal of Medicine, 1993, vol. 329, No. 20, p. 1456-1462.*
Manjunath et al. Post Graduate Medicine, 2001, vol. 110, No. 6, pp. 1-13.*
BIOCON-press release, May 1, 2003, pp. 1-2.*
EUCLID Study, Lancet, 1997, vol. 349, pp. 1787-1792.*
Webster Ninth New Collegiate Dictionary. 2000, Definition of Prevention p. 1.*
Webster Ninth New Collegiate Dictionary. 2000, Definition of Halt, p. 1.*
Rossing et al. Diabetes, 1997, vol. 46, Issue 3, pp. 481-487.*
Hao, et al., "Mycophenolate Mofetil Can Prevent the Development of Diabetes in BB Rats" *Ann. NY Acad. Sci.* 696: 328-332, 1993.
Remuzzi, et al., "Combining an Antiproteinuric Approach with Mycophenolate Mofetil Fully Suppresses Progressive Nephropathy of Experimental Animals", *J. Am. Soc. Nephrol.*, 10: 1542-1549, 1999.
Utimura, et al., "Mycophenolate Mofetil Prevents the Development of Glomerular Injury in Experimental Diabetes", *Kidney International*, 63: 209-216, 2003.
Dooley, M., et al., "Mycophenolate Mofetil Therapy in Lupus Nephritis: Clinical Observations" *J. American Soc. Nephrology* 10:4 833-839, 1999.

* cited by examiner

*Primary Examiner*—Sreeni Padmanabhan
*Assistant Examiner*—Samira Jean-Louis
(74) *Attorney, Agent, or Firm*—Choate, Hall & Stewart LLP; Andrea L. C. Robidoux

(57) ABSTRACT

The present invention relates to a method of treating diabetic nephropathy with a combination of an immunosuppressive agent and an ACE inhibitor.

3 Claims, 5 Drawing Sheets

Group I – Lisinopril ( completed)

Group II – MMF ( completed)

Group III – MMF + Lisinopril ( completed)

Secondary Efficacy parameter – Estimated GFR

| SI No | Patient No | V1 | V2 | V3 | V4 | V5 | V6 |
|---|---|---|---|---|---|---|---|
| 3 | 3 | 81.9 | 88.2 | 93.1 | 88 | 95.4 | 80.7 |
| 12 | 68 | 68.6 | 68.6 | 68.2 | 75.9 | 77.1 | 75.6 |
| 21 | 147 | 52 | 56.8 | 52.03 | 52 | 69.4 | 56.8 |

Group III – MMF + Lisinopril (completed)

MYCOPHENOLATE MOFETIL IN DIABETIC NEPHROPATHY

CROSS REFERENCE TO RELATED APPLICATIONS

This application is a continuation-in-part and claims priority under 35 U.S.C. §120 to co-pending PCT application number PCT/IN2004/000123, filed May 5, 2004, which claims priority to Indian patent application number 377/Mas/2003, filed May 5, 2003, the entirety of each of which are hereby incorporated herein by reference.

FIELD OF THE INVENTION

The present invention is in the field of medicinal chemistry and relates to a combination of an immunosuppressive agent and an ACE inhibitor. The present invention also provides pharmaceutically acceptable compositions thereof and methods of using the same.

BACKGROUND OF THE INVENTION

Diabetes mellitus is one of the common systemic diseases affecting the kidneys, often resulting in diabetic nephropathy. In fact, diabetic nephropathy will likely develop in a third of those patients who have had type 1 diabetes for more than 20 years. Diabetic nephropathy typically affects the network of tiny blood vessels (the microvasculature) in the glomerulus, a key structure in the kidney composed of capillary blood vessels. The glomerulus is critically necessary for the filtration of the blood. Features of diabetic nephropathy include the nephrotic syndrome with excessive filtration of protein into the urine (proteinuria), high blood pressure (hypertension), and progressively impaired kidney function. When it is severe, diabetic nephropathy leads to kidney failure, end-stage renal disease, and the need for chronic dialysis or a kidney transplant.

The involvement of diabetes in diabetic nephropathy is essentially glomerular. The primary pathogenic role of hyperglycemia in diabetic renal disease is so well established that diabetic nephropathy is today considered as hyperglycemic glomerulopathy. Mortality and morbidity in these patients is often due to cardiovascular disease, probably accelerated by hypertension and hyperlipidemia. Biochemical, hormonal, immunological and rheological factors have been shown to be etiologically important in the pathogenesis of diabetic nephropathy. The biochemical factors implicated include hyperglycemia and glycosylated proteins in blood and basement membrane of the kidneys. Also, there is experimental and clinical evidence to suggesting that recruitment of monocytes into glomeruli may play a role in the pathogenesis of this diabetic complication.

Diabetes mellitus accounts for about one-third of all end-stage renal disease. The landmark study by Lewis et. al. 1993 demonstrates that, in patients with type 1 diabetes mellitus and diabetic nephropathy, Captopril prevents or delays the progression of renal disease. These findings are have been generalized to other Angiotensin Converting Enzyme inhibitors (ACE inhibitors) and to patients with both type 1 and type 2 diabetes regardless of baseline renal function or arterial blood pressure (Ravid et. al. 1993, 1996). In addition to preventing diabetic nephropathy, ACE inhibitors also may decrease retinopathy progression in type 1 diabetics (Chaturvedi et. al. 1998).

Several mechanisms participate in the renal protection afforded by ACE inhibitors. Increased glomerular capillary pressure induces glomerular injury, and ACE inhibitors reduce this parameter both by decreasing arterial blood pressure and by dilating renal efferent arterioles. Because angiotensin II is a growth factor, reductions in the intrarenal levels of angiotensin II may further attenuate mesangial cell growth and matrix production.

Mycophenolate mofetil (MMF) is prodrug that is rapidly hydrolyzed to mycophenolic acid (MPA), a selective, uncompetitive, and reversible inhibitor of inosine monophosphate dehydrogenase (IMPDH). IMPDH is an important enzyme in the de novo pathway of guanine nucleotide synthesis. B and T lymphocytes are highly dependent on this pathway for cell proliferation, while other cell types can use salvage pathways. MPA therefore selectively inhibits lymphocyte proliferation and functions, including antibody formation, cellular adhesion, and migration. The effects of MPA on lymphocytes can be reversed by adding guanosine or deoxyguanosine to the cells (Krensky et. al. 2001).

MMF ameliorates the renal lesions in several models of experimental glomerular disease. The ability of MMF to suppress not only the immune response, but also smooth cell proliferation, makes the drug a candidate for preventing renal fibrosis. This is because myofibrobalsts share many features with vascular smooth muscle cells. Preliminary results suggest that MMF is effective in several types of glomerulonephritis after conventional therapy had failed (Badid et. al. 2001).

Two recent studies have evaluated the impact of MMF in patients with IgA nephropathy. Preliminary results from both of these studies were presented at the 2001 Annual Meeting of the American Society of Nephrology (Chen et. al. 2001 and Maes et. al. 2001). Chen et al, from China, compared the effect of MMF Vs Prednisone in 62 patients. The age of these patients ranged from 9-54 years and each of the patients had protein excretion rates >2g per day. The dose of the MMF given to the patients varied from 1-1.5g per day whereas a control group received 30-40 mg of Prednisone per day. Fifteen patients in each of the groups had been followed for seventy two weeks. Whereas both groups of patients showed reduction of proteinuria after 3 and 6 months, the decrease in the MMF patients was greater after 6 months. This decrease in proteinuria continued in the MMF group through 72 weeks. Chen, et al concluded in this preliminary report that MMF was superior to Prednisone in decreasing proteinuria, protecting renal function and also decreasing blood lipid levels.

With most immunosuppressive agents, increasing the degree of immunosuppression increases the likelihood of side effects of immunosuppression, including infection and bone marrow suppression. However, experience from controlled clinical trials in renal transplantation shows that MMF may be an exception to this generalization because the MMF-treated patients were able to achieve a greater degree of immunosuppression yet suffered little increase in the incidence of infection or bone marrow suppression (Dooley et. al. 1999).

Dooley and his coworkers concluded in their study that MMF is well tolerated and has possible efficacy in controlling major renal manifestation of systemic lupus erythomatosis. In lupus nephritis, these authors found that 0.5 to 1.5 g/d dose of MMF were sufficient. Miller et. al. 2000 in their study of mycophenolate mofetil use in resistant membranous nephropathy, used 0.5 to 2.0 g/d dose of MMF. The dose of MMF was titrated according to leukocyte counts and side effects, in most cases because of gastrointestinal symptoms.

The most obvious endpoint for treatment failure in patients with diabetic nephropathy is progression to end stage renal disease (ESRD). However, since the period from diagnosis to ESRD in diabetic nephropathy patients with normal renal function at onset may be over 10 years. Only about 30% of diabetics live for 10 years beyond the onset of clinical proteinuria. The degree of diabetes control is a necessary component, but is not linearly related to the development of renal failure. Control of hyperglycemia may become very difficult in nephropathic diabetic. Normalizing the blood pressure at every stage of progressive diabetic renal disease is stressed as an important component of the therapeutic program. Apart from the control of systemic hypertension, control of intraglomerular hypertension is also considered important in diabetic nephropathy. ACE inhibitors have been shown to lower the intraglomerular hypertension and thus reduce hyperfiltration of diabetic nephropathy. It is therefore, recommended that in diabetics with even normal blood pressure, ACE inhibitors be given to lower intraglomerular pressure.

It was reported that mycophenolate mofetil prevents the development of glomerular injury in experimental diabetes (Utimura et. al. 2003). Diabetic rats exhibited marked glomerular hyperfiltration and hypertension. They developed progressive albuminuria and exhibited widespread glomerulosclerotic lesions associated with macrophage infiltration at 8 months. Treatment with MMF had no effect on blood pressure, glomerular dynamics or blood glucose levels, but did prevent albuminuria, glomerular macrophage infiltration and glomerulosclerosis.

In light of the above, there remains an unmet need for therapies for treating diabetic nephropathy and its related symptoms.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF CERTAIN EMBODIMENTS OF THE INVENTION

Uses and Methods

Figure 1:
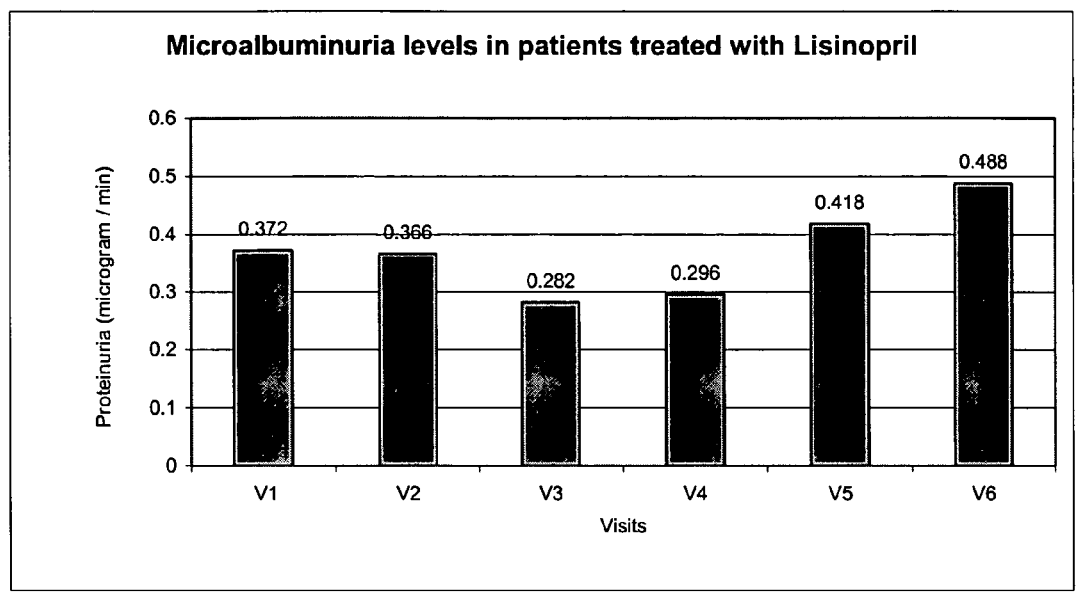
FIG. 1 depicts the average microalbuminuria levels at each visit in patients who have completed their treatment with lisinopril.

Diabetic nephropathy is a clinical syndrome characterized by persistent albuminuria (>300 mg/d or >200 mcg/min) combined with a relentless decline in the glomerular filtration rate (GFR). Elevated arterial blood pressure is also commonly associated with diabetic nephropathy.

In addition, three major histologic changes occur in the glomeruli of persons with diabetic nephropathy. First, mesangial expansion is directly induced by hyperglycemia, perhaps via increased matrix production or glycosylation of matrix proteins. Second, GBM thickening occurs. Third, glomerular sclerosis is caused by intraglomerular hypertension (induced by renal vasodilatation or from ischemic injury induced by hyaline narrowing of the vessels supplying the glomeruli). These different histologic patterns appear to have similar prognostic significance.

Without being bound by theory, it is believed that hyperglycemia (causing hyperfiltration and renal injury), advanced glycosylation products, and activation of cytokines play a role in the onset of diabetic nephropathy. Hyperglycemia increases the expression of transforming growth factor-beta (TGF-beta) in the glomeruli and of matrix proteins specifically stimulated by this cytokine. TGF-beta may contribute to both the cellular hypertrophy and enhanced collagen synthesis observed in persons with diabetic nephropathy.

It has been surprisingly found that a combination of an immunosuppressive agent and an inhibitor of angiontensin converting enzyme (ACE) is especially useful for treating, or lessening the severity of, diabetic nephropathy. Accordingly, the present invention provides a method for treating, or lessening the severity of, diabetic nephropathy in a patient in need thereof, wherein said method comprises administering to said patient a combination of an immunosuppressive agent and an inhibitor of angiontensin converting enzyme (ACE).

Suitable immunosuppressive agents useful for the present invention include IMPDH inhibitors, such as mycophenolate mofetil. Other suitable immunosuppressive agents useful for the present invention are known in the art and include cyclosporins, rapamycyins, FK-506 and derivatives thereof, and mizoribine, among others.

Suitable ACE inhibitors useful for the present invention include lisinopril, captopril, ramipril, enalapril, and quinopril, among others.

According to one aspect of the present invention, said method for treating, or lessening the severity of, diabetic nephropathy comprises administering to a patient in need thereof a combination of mycophenolate and an ACE inhibitor. Yet another embodiment provides a method for treating, or lessening the severity of, diabetic nephropathy wherein said method comprises administering to a patient in need thereof a combination of an immunosuppressive agent and lisinopril. In certain embodiments, the present invention provides a method for treating, or lessening the severity of, diabetic nephropathy wherein said method comprises administering to a patient in need thereof a combination of mycophenolate mofetil and lisinopril.

Diabetic nephropathy is often characterized by a continual decline in glomerular filtration rate (GFR). Typically, a normal GFR is from about 100 to about 140 milliliters per minute. However, a GFR of <75 milliliters per minute is a sign of advanced nephropathy and a GFR of <10 milliliters per minute is often considered "end-stage" renal disease. Accordingly, another aspect of the present invention provides a method for slowing the decline in GFR in a patient in need thereof wherein said method comprises administering to said patient a combination of an immunosuppressive agent and an ACE inhibitor. In other embodiments, the present invention provides a method for slowing the decline in GFR in a patient in need thereof wherein said method comprises administering to said patient a combination of an immunosuppressive agent and lisinopril. In still other embodiments, the present invention provides a method for slowing the decline in GFR in a patient in need thereof wherein said method comprises administering to said patient a combination of mycophenolate mofetil and an ACE inhibitor. In certain embodiments, said method comprises administering a combination of mycophenolate mofetil and lisinopril.

Yet another aspect of the present invention provides a method for halting the decline in GFR in a patient in need thereof wherein said method comprises administering to said patient a combination of an immunosuppressive agent and an ACE inhibitor. In certain embodiments, the present invention provides a method for halting the decline in GFR in a patient in need thereof wherein said method comprises administering to said patient a combination of mycophenolate mofetil and an ACE inhibitor. In other embodiments, the present method comprises administering a combination of an immunosuppressive agent and lisinopril. In yet other embodiments, the present method comprises administering a combination of mycophenolate mofetil and lisinopril.

Still another aspect of the present invention provides a method for reversing the decline in GFR in a patient in need thereof wherein said method comprises administering to said patient a combination of an immunosuppressive agent and an ACE inhibitor. In other aspects, the present invention provides a method for reversing the decline in GFR in a patient in need thereof wherein said method comprises administering to said patient a combination of an immunosuppressive agent and lisinopril. In yet other aspects, said method comprises administering a combination of mycophenolate mofetil and an ACE inhibitor. In still other aspects, said method comprises administering a combination of mycophenolate mofetil and lisinopril.

According to yet another aspect, the present invention provides a method of preventing a decline in GFR in a patient in need thereof wherein said method comprises administering to said patient a combination of an immunosuppressive agent and an ACE inhibitor. In other embodiments, said method comprises administering a combination of myophenolate mofetil and an ACE inhibitor. In still other embodiments, said method comprises administering a combination of an immunosuppressive agent and lisinopril. According to yet other embodiments, said method comprises administering a combination of mycophenolate mofetil and lisinopril.

Diabetic nephropathy is also characterized by the presence of protein in the urine. This is known as proteinuria. Typically, a 24-hour urine collection containing more than 150 mg of protein is abnormal whereas significant proteinuria may exceed 300-500 mg per day. Thus, according to certain embodiments, the present invention provides a method of decreasing proteinuria in a patient in need thereof wherein said method comprises administering to said patient a combination of an immunosuppressive agent and an ACE inhibitor. Another aspect of the present invention provides a method for decreasing proteinuria in a patient in need thereof wherein said method comprises administering to said patient a combination of mycophenolate mofetil and an ACE inhibitor. Still another aspect of the present invention provides a method for decreasing proteinuria in a patient in need thereof wherein said method comprises administering to said patient a combination of an immunosuppressive agent and lisinopril. Yet another aspect of the present invention provides a method for decreasing proteinuria in a patient in need thereof wherein said method comprises administering to said patient a combination of mycophenolate mofetil and lisinopril.

As used herein, the phrase "decreasing proteinuria" refers to the amount of proteinuria in a patient after administering a combination of the present invention wherein the patient administered a combination of the present invention has a lower amount of proteinuria as compared with the patient prior to the administration of a combination of the present invention. It will be appreciated that the detection of proteinuria by a 24-hour urine collection is performed by methods known in the art, such as a 24-hour urine collection.

Yet another aspect of the present invention provides a method for decreasing proteinuria and increasing GFR in a patient in need thereof wherein said method comprises administering to said patient a combination of an immunosuppressive agent and an ACE inhibitor. In certain embodiments, the present invention provides a method for decreasing proteinuria and increasing GFR in a patient in need thereof wherein said method comprises administering to said patient a combination of mycophenolate mofetil and an ACE inhibitor. In other embodiments, the present invention provides a method for decreasing proteinuria and increasing GFR in a patient in need thereof wherein said method comprises administering to said patient a combination of an immunosuppressive agent and lisinopril. In still other embodiments, the present invention provides a method for decreasing proteinuria and increasing GFR in a patient in need thereof wherein said method comprises administering to said patient a combination of mycophenolate mofetil and lisinopril.

Systemic Lupus Erythematosus (SLE), also known as lupus, is an autoimmune disease lasting many years. It is common for Lupus to affect the kidneys resulting in lupus nephropathy. Thus, another aspect of the present invention provides a method of treating, or lessening the severity of, lupus nephropathy wherein said method comprises administering to a patient in need thereof a combination of an immunosuppressive agent and an inhibitor of angiontensin converting enzyme (ACE). In certain embodiments, said method for treating, or lessening the severity of, lupus nephropathy comprises administering to a patient in need thereof a combination of mycophenolate and an ACE inhibitor. Yet another embodiment provides a method for treating, or lessening the severity of, lupus nephropathy in a patient in need thereof, wherein said method comprises administering to said patient a combination of an immunosuppressive agent and lisinopril. In other embodiments, the present invention provides a method for treating, or lessening the severity of, lupus nephropathy in a patient in need thereof, wherein said method comprises administering to said patient a combination of mycophenolate mofetil and lisinopril.

Pharmaceutically Acceptable Compositions

As discussed above, the present invention provides a combination of an immunosuppressant and an ACE inhibitor, as defined and described in embodiments above and herein, useful for the treatment of diabetic nephropathy. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

In certain embodiments, the immunosuppressant and ACE inhibitors of the present invention are administered together in the same composition to a patient in need thereof. In an alternate embodiment, the immunosuppressant and ACE inhibitors of the present invention are administered separately to a patient in need thereof. When these agents are administered separately they may be administered to the patient sequentially or simultaneously.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, the methods of the present invention, as described above and herein, for the treatment or lessening the severity of nephropathy and its symptoms also comprise administering an effective amount of a pharmaceutically acceptable composition of the present invention to a patient in need thereof. In certain embodiments of the present invention an "effective amount" of the compound or pharmaceutically acceptable composition is that amount effective for treating or lessening the severity of diabetic nephropathy. The compounds and compositions, according to the method of the present invention, may be administered using any amount and any route of administration effective for treating or lessening the severity of diabetic nephropathy. The exact amount required will vary from subject to subject, depending on the species, age, and general condition of the subject, the severity of the infection, the particular agent, its mode of administration, and the like. The compositions of the invention are preferably formulated in dosage unit form for ease of administration and uniformity of dosage.

The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the diabetic nephropathy being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Major therapeutic interventions for diabetic nephropathy include blood glucose control, antihypertensive treatment, and restriction of dietary proteins. Accordingly, the combined therapy of the present invention may also be administered in combination with known therapies for treating diabetes. In certain embodiments, the compounds of the present invention, and pharmaceutically acceptable compositions thereof, can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a combination of the present invention may be administered concurrently with another agent used to treat the same disorder), or they may achieve different effects (e.g., control of any adverse effects).

For example, agents for treating diabetes may be combined with the compounds and compositions of this invention. Such agents include, but are not limited to, insulin and insulin analogues in injectable or inhalation form, glitazones, alpha glucosidase inhibitors, biguanides, insulin sensitizers, and sulfonyl ureas.

Other examples of agents the compounds of this invention may also be combined with include, without limitation, agents for treating cardiovascular disease such as beta-blockers, diuretics, nitrates, calcium channel blockers, and statins.

In certain embodiments, the compounds and compositions of the present invention are utilized in combination with other therapies normally employed to treat nephropathy, such as dialysis and kidney transplantation.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In an alternate embodiment, the methods of this invention that utilize compositions that do not contain an additional therapeutic agent, comprise the additional step of separately administering to said patient an additional therapeutic agent.

When these additional therapeutic agents are administered separately they may be administered to the patient prior to, sequentially with or following administration of the compositions of this invention.

In order that the invention described herein may be more fully understood, the following examples are set forth. It should be understood that these examples are for illustrative purposes only and are not to be construed as limiting this invention in any manner.

EXAMPLES

1. Definitions

As used herein, the term "Efficacy Endpoints" refers to the parameters which represent the measure of the drugs ability to improve the signs and/or symptoms of the disease.

As used herein, the term "Safety Endpoints" refers to the parameters, which represent any incidence of adverse events and in particular the serious adverse events that may be associated with the use of the drug treatment for diabetic nephropathy.

As used herein, the term "MMF" refers to mycophenolate mofetil.

As used herein, the term "ACE inhibitor" in the present invention means any drug or molecule that inhibit Angiotensin Converting Enzyme (ACE) including, but not limited to, lisinopril, captopril, quinapril, and enalapril.

As used herein, the term "Micral test" refers to a measure of albumin excretion rate in urine.

As used herein, the term "V1" represents the first visit of the patient during which the patient is screened for eligibility to participate in the trial for treatment of diabetic nephropathy.

As used herein, the term "V2" represents the second visit of the patient during which the patient is subjected to treatment with either MMF or lisinopril alone or in combination of both.

As used herein, the term "V3" represents the third visit of the patient one month after initialization of the treatment [V2].

As used herein, the term "V4" represents the fourth visit of the patient three months after initialization of the treatment [V2].

As used herein, the term "V5" represents the fifth visit of the patient six months after initialization of the treatment [V2].

As used herein, the term "V6" represents the sixth visit 9 months after initialization of the treatment [V2]; patients are monitored to determine if they show any changes in estimated GFR or urine protein/creatinine ratios after treatment has been discontinued and after completion of which the end of trial form is filled.

2. Design of the Experiment

The study of the effect of MMF and lisinopril for the treatment of diabetic nephropathy was designed in the following manner.

Sample Size:

In this study, a total of 30 patients were planned of which 18 were randomized and subjected to enter into one of the studies in which the patient groups each received MMF alone, lisinopril alone, or a combination of both MMF and lisinopril.

Efficacy End Points:

The primary end-point for this study was the proteinuria value obtained from the patients via 24-hour urine protein which was measured using the Calorimetric method Pyrogallol Red/SDS liquid stable single reagent.

A secondary end-point for this study was the GFR value obtained for each patient. This Secondary Endpoint included Estimated GFR, which was calculated using the following formulae:

Measurement of GFR

Once all data was collected, Glomerular Filtration Rate GFR) was determined by the Cockcroft-Gault formula.

For Women -

Estimated GFR (in ml/min) =
[140 −age (in years) * weight (in Kg)
Serum Creatinie level (in μmol/L)

For Men -

Estimated GFR (in ml/min) =
1.23 * [140 −age (in years) * weight (in Kg)
Serum Creatinie level (in μmol/L)

Safety Endpoints:

In this study, the patients were evaluated for adverse events, physical examination; vital signs, hematology and clinical biochemistry.

Selection Criteria

1. Inclusion Criteria

The inclusion of a patient is based on the following criteria. Type 1 and type 2 diabetic patients; male and postmenopausal (Natural & surgical) female diabetic patients; age 18-65 years; micral test positive (albumin excretion rate 20-200 μgm/min); patient must be able to swallow the oral medications to be used in the study; patient must sign an informed consent prior to the study.

2. Exclusion Criteria

The exclusion of a subject from the study is based on the following criteria: Premenopausal female patients of any age; clinical evidence of SLE; uncontrolled diabetes (Fasting Blood Glucose $\geq$160 mg/dl or HbA1c $\geq$7.5%); uncontrolled hypertension (Systolic blood pressure $\geq$160 mm Hg and/or diastolic blood pressure $\geq$100 mm Hg); impaired renal function with serum creatinine $\geq$1.4 mg/dl; well-documented history of Henoch-Schonlein Purpura (with an exception to previous non-specific abdominal pain or rash—which is not an exclusion criteria); clinical evidence of cirrhosis or chronic active liver disease; abnormal laboratory values at the time of study entry; absolute neutrophil count (ANC) <2000/nm$^3$, or hematocrit (HCT) <28%; AER >200 μgm/min; BUN $\geq$25 mg/dl; known contraindication or allergy to the administration of MMF or lisinopril; history of significant gastrointestinal disorder, e.g. severe chronic diarrhea or active peptic ulcer disease; active systemic infection or history of serious infection within one month of entry; known infection with HIV, hepatitis B or hepatitis C; other major organ system disease or malignancy other than skin cancer fully excised more than 5 years prior to entry; current or prior treatment with MMF or azathioprine; current or recent (within 30 days) exposure to any investigational drug.

Study Design:

Evaluation of the effects of MMF or ACE inhibitors alone or in combination on the status of proteinuria in patients with diabetic nephropathy was an open-labeled, randomized study. This study consisted of three arms as shown below.

1. treatment with MMF alone
2. treatment with combination of MMF and lisinopril
3. treatment with lisinopril alone In addition, there were three phases of the study as shown below.

Phase 1: Screening Phase (Duration 1 to 4 weeks): 303 patients were screened on their first visit (V1), based on the given inclusion and exclusion criteria to determine if they were eligible for the study and to assess likelihood of compliance with study protocol. Micral test for every patient was done to determine the eligibility.

Phase 2: Treatment Phase (6 months): Every patient who qualified the screening phase was assigned one of the treatment arms. During this phase, patients were monitored closely and efficacy and safety parameters are assessed every month.

The patients were withdrawn from the study if any of the following are observed: ingestion of prohibited medication; serious adverse event; persistent gastrointestinal disorder of moderate severity after MMF dose; hematocrit persistently lower than 25% after MMF dose; ANC persistently lower than 1500/mm$^3$ after MMF; ANC lower than 1000/mm$^3$ at any time; administration of live oral vaccine; patient withdrawal of consent to participate; patient is moving out of the area of the location of the study center; interruptions of MMF treatment totaling 28 days or more cumulatively, or any single interruption of more than 21 consecutive days; inability to tolerate lisinopril Phase 3: Post-treatment Phase (3 months): During this phase, patients were monitored carefully to determine if they showed any changes in estimated GFR or urine protein/creatinine ratios after treatment had been discontinued.

Study Products and Dosage:
1. MMF: The dose of MMF given during the study was 500 mg per oral twice a day throughout the study.
2. Lisinopril: The starting dose of lisinopril given in the study was 5 mg per oral twice a day. In case of hypertensive patients, the dose could be titrated upwards based on investigator's discretion, which in turn was based on the patient's "safety end point".
3. MMF+Lisinopril: In the patients who received both the drugs, the dose of MMF was 500 mg per oral twice a day and lisinopril was 5 mg per oral twice a day. In the case of hypertensive patients, the dose of lisinopril could be titrated upwards based on investigator's discretion, which in turn was based on the patient's "safety end point".

Results 19 male & 11 female patients were selected at visit no. 1 [VI] with type 1 and type 2 diabetes for the trial between the age group of 18-65 years who show positive Micral test (albumin excretion rate 20-200 μgm/min).

Example 1

The values of base line lab parameters such as 24 hour urine protein and estimated GFR were obtained from the patients in visit no. 2 [V2] prior to treatment with MMF. The values of the parameters in V2 were compared against the values obtained at visit 3 [V3], which is scheduled 1 month from V2. It was found that MMF, after 1 month of treatment, reduced proteinuria in 67% of the patients. The effect of the treatment with MMF alone, on proteinuria, after 1 month is disclosed in the table immediately below.

| Patients status | At baseline-V2 prior to treatment Mean | | 1 month after treatment at V3 Mean | | Result Difference | |
|---|---|---|---|---|---|---|
| | 24 h Urine protein | GFR | 24 h Urine protein | GFR | 24 h Urine protein | GFR |
| Benefited | 316.66 | 89.03 | 112.73 | 89.3 | −203.93 | 0.27 |
| Not benefited | 334.3 | 70.86 | 696.3 | 75.26 | 361.7 | 4.40 |

Example 2

The values of base line lab parameters such as 24 hour urine protein and estimated GFR were obtained from the patients at V2 prior to treatment with MMF. The values of the parameters in V2 were compared against the values obtained at V3, which was scheduled 3 months from V2 during which patients received 500 mg of MMF twice daily. MMF treatment at V4 at the end of 3 months reduced proteinuria in 67% of the patients. The effect of the treatment with MMF alone, on proteinuria, after 3 months is disclosed in the table immediately below.

| Patients status | prior to treatment at baseline-V2 Mean | | 3 month after treatment at V4 Mean | | Result Difference | |
|---|---|---|---|---|---|---|
| | 24 h Urine protein | GFR | 24 h Urine protein | GFR | 24 h Urine protein | GFR |
| Benefited | 397.4 | 83.2 | 260.8 | 81.85 | −136.6 | −1.35 |
| Not benefited | 249.9 | 56.4 | 305.5 | 49.9 | | 49.9 |

Example 3

Figure 2:
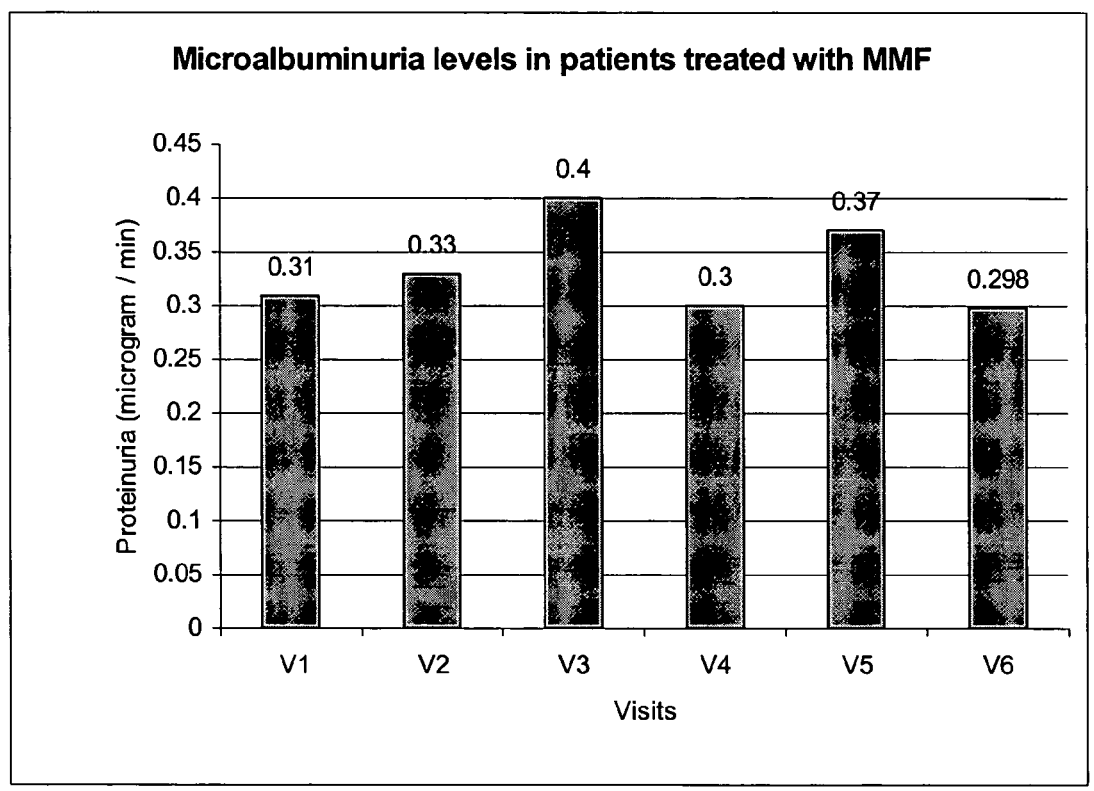
FIG. 2 depicts the average microalbuminuria levels at each visit in patients who have completed their treatment with mycophenolate mofetil (MMF).

The values of base line lab parameters such as 24 hour urine protein and estimated GFR were obtained from the patients at V2 prior to treatment with MMF. The values of the parameters in V2 were compared against the values obtained at V3, V4, V5, and V6 during which patients received 500 mg of MMF twice daily. The effect of the treatment with MMF alone, on proteinuria, over 9 months is depicted in FIG. 2.

Example 4

The values of base line lab parameters such as 24 hour urine and estimated GFR were obtained from the patients at V2 prior to treatment with lisinopril. The values of the parameters at V2 were compared against the values obtained at V3, which was scheduled 1 month from V2, during which patients received 5 mg of lisinopril twice daily. Lisinopril treatment at the end of 1 month reduced proteinuria in 42% of the patients. The effect of the treatment with lisinopril alone, on proteinuria, after 1 month is disclosed in the table immediately below.

|  | At baseline-V2 prior to treatment Mean | | 1 month after treatment at V3 Mean | | Result Difference | |
|---|---|---|---|---|---|---|
| Patients status | 24 h Urine protein | GFR | 24 h Urine protein | GFR | 24 h Urine protein | GFR |
| Benefited | 370.26 | 79.36 | 236.66 | 79.16 | −133.6 | −0.09 |
| Not benefited | 156.52 | 62.07 | 211.25 | 63.97 | 53.73 | 1.91 |

Example 5

The values of base line lab parameters such as 24 hour urine protein and estimated GFR were obtained from the patients at V2 prior to treatment with lisinopril. The values of the parameters at V2 were compared against the values obtained at V4, which was scheduled 3 month from V2, during which patients received 5 mg of lisinopril twice daily. Lisinopril treatment at the end of 3 month reduced proteinuria in 40% of the patients. The effect of the treatment with lisinopril alone, on proteinuria, after 3 months is disclosed in the table immediately below.

|  | At baseline-V2 prior to treatment Mean | | 3 month after treatment at V4 Mean | | Result Difference | |
|---|---|---|---|---|---|---|
| Patients status | 24 h Urine protein | GFR | 24 h Urine protein | GFR | 24 h Urine protein | GFR |
| Benefited | 429.9 | 81.6 | 161.15 | 89.55 | −268.75 | 7.95 |
| Not benefited | 187.73 | 68.63 | 289.2 | 68.76 | 101.47 | 0.13 |

Example 6

The values of base line lab parameters such as 24 hour urine and estimated GFR were obtained from the patients at V2 prior to treatment with lisinopril. The values of the parameters at V2 were compared against the values obtained at V5, which was scheduled 6 month from V2, during which patients received 5 mg of lisinopril twice daily. Lisinopril treatment at the end of 6 month reduced proteinuria in 50% of the patients. The effect of the treatment with lisinopril alone, on proteinuria, after 6 months is disclosed in the table immediately below.

|  | At baseline-V2 prior to treatment Mean | | 6 month after treatment at V5 Mean | | Result Difference | |
|---|---|---|---|---|---|---|
| Patients status | 24 h Urine protein | GFR | 24 h Urine protein | GFR | 24 h Urine protein | GFR |
| Benefited | 488 | 77.4 | 248.4 | 105.9 | −239.6 | 28.5 |
| Not benefited | 371.8 | 85.8 | 626 | 76.4 | 254.2 | −9.4 |

Example 7

The values of base line lab parameters such as 24 hour urine protein and estimated GFR were obtained from the patients at V2 prior to treatment with lisinopril. The values of the parameters in V2 were compared against the values obtained at V3, V4, V5, and V6 during which patients received 5 mg of lisinopril twice daily. The effect of the treatment with lisinopril alone, on proteinuria, over 9 months is depicted in FIG. 1.

Example 8

The values of base line lab parameters such as 24 hour urine protein and estimated GFR were obtained from the patients at V2 prior to treatment with the combination of MMF and lisinopril. The patients were treated with 500 mg of MMF twice daily along with lisinopril 5 mg twice daily. The values of the parameters in V2 were compared against the values obtained at V3, which was scheduled 1 month from V2. MMF and lisinopril combination treatment at the end of 1 month of treatment reduced proteinuria in 75% of the patients. The effect of the treatment with a combination of MMF and lisinopril, on proteinuria, after 1 month is disclosed in the table immediately below.

|  | At baseline-V2 prior to treatment Mean | | 1 month after treatment at V3 Mean | | Result Difference | |
|---|---|---|---|---|---|---|
| Patients status | 24 h Urine protein | GFR | 24 h Urine protein | GFR | 24 h Urine protein | GFR |
| Benefited | 426.6 | 72.36 | 280.96 | 70.04 | −145.63 | −2.31 |
| Not benefited | 183.3 | 68.6 | 225 | 68.2 | 41.7 | −0.4 |

Example 9

The values of base line lab parameters such as 24 hour urine protein, urine protein/creatinine ratio and estimated GFR were obtained from the patients at V2 prior to treatment with the combination of MMF and lisinopril. The patients were treated with 500 mg of MMF twice daily along with lisinopril 5 mg twice daily. The values of the parameters in V2 were compared against the values obtained at V4, which was scheduled 3 months from V2. MMF and lisinopril combination treatment at the end of 3 months of treatment reduced proteinuria in 100% of the patients. The effect of the treatment with a combination of MMF and lisinopril, on proteinurea, after 3 months is disclosed in the table immediately below.

|  | At baseline-V2 prior to treatment Mean | | 3 month after treatment at V3 Mean | | Result Difference | |
|---|---|---|---|---|---|---|
| Patients status | 24 h Urine protein | GFR | 24 h Urine protein | GFR | 24 h Urine protein | GFR |
| Positive | 287.6 | 91.1 | 228.7 | 81.95 | −58.85 | −9.15 |

Example 10

The values of base line lab parameters such as 24 hour urine protein, urine protein/creatinine ratio and estimated GFR were obtained from the patients at V2 prior to treatment with the combination of MMF and lisinopril. The patients were treated with 500 mg of MMF twice daily along with lisinopril 5 mg twice daily. The values of the parameters in V2 were compared against the values obtained at V5, which was scheduled 6 months from V2. MMF and lisinopril combination treatment at the end of 6 months of treatment reduced proteinuria in 100% of the patients. The effect of the treatment with a combination of MMF and lisinopril, on proteinuria, after 9 months is disclosed in the table immediately below.

| Patients status | At baseline-V2 prior to treatment Mean | | 3 month after treatment at V3 Mean | | Result Difference | |
|---|---|---|---|---|---|---|
| | 24 h Urine protein | GFR | 24 h Urine protein | GFR | 24 h Urine protein | GFR |
| Positive | 392 | 113.6 | 364 | 119.6 | −28 | 6 |

Example 11

Figure 3:
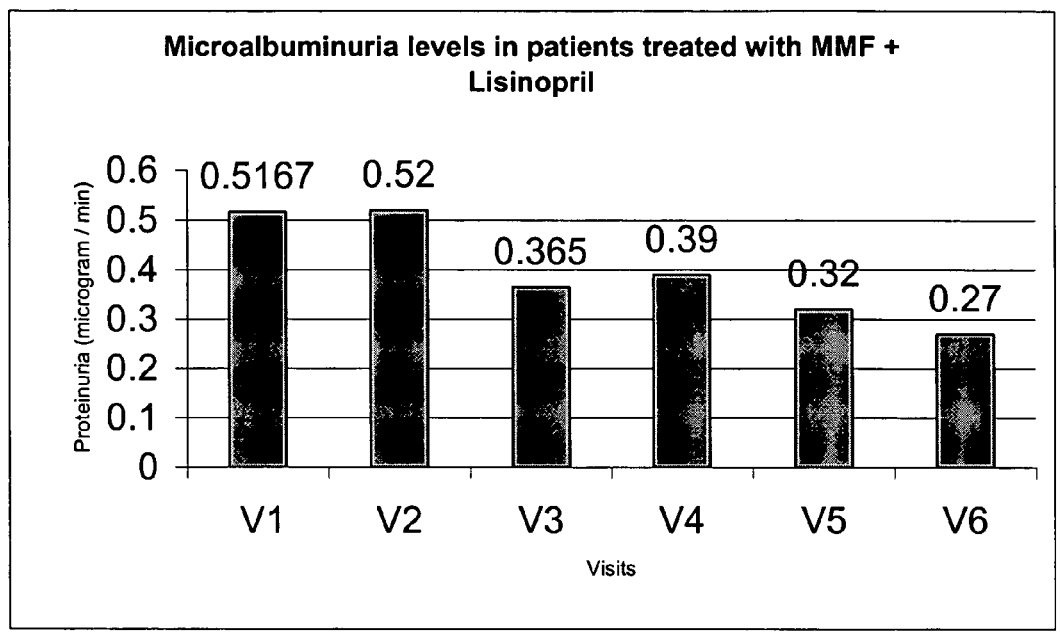
FIG. 3 depicts the average microalbuminuria levels at each visit in patients who have completed their treatment with MMF and lisinopril showing a decreasing trend.
Figure 4:
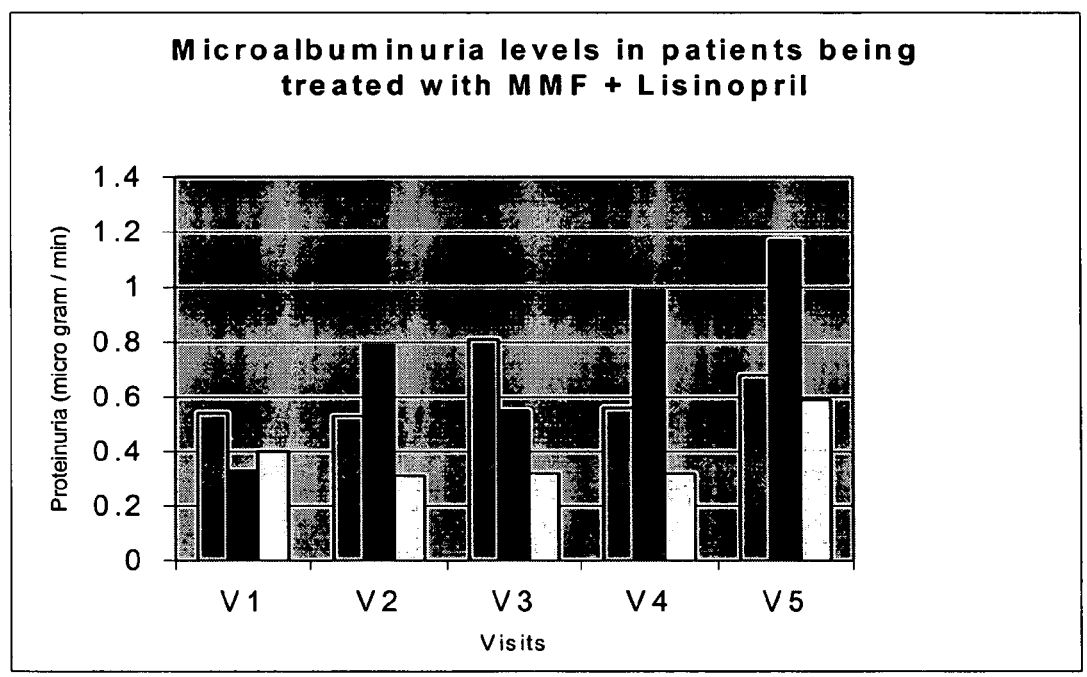
FIG. 4 depicts the proteinuria measurements obtained from three patients at each individual visit who are on MMF and lisinopril combination therapy.
Figures 5A, 5B:
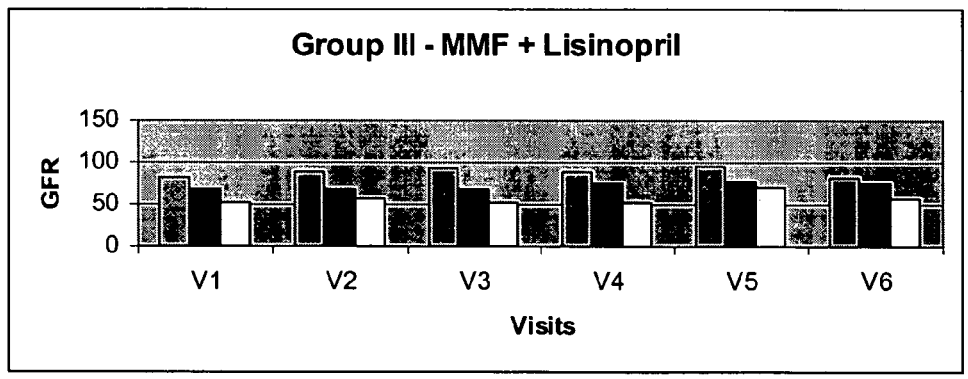
FIG. 5a depicts the estimated GFR values of patients in the study.
FIG. 5b depicts the actual GFR values obtained from patients administered a combination of mycophenolate mofetil and linisopril over 6 months.

The values of base line lab parameters such as 24 hour urine protein and estimated GFR were obtained from the patients at V2 prior to treatment with a combination of MMF and lisinopril. The values of the parameters in V2 were compared against the values obtained at V3, V4, V5, and V6 during which patients received 500 mg of MMF twice daily along with 5 mg of lisinopril twice daily. The effect of the treatment with a combination of MMF and lisinopril, on proteinuria, over 9 months is depicted in FIG. 3.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method for treating, or lessening the severity of, diabetic nephropathy in an adult human patient in need thereof, wherein said method comprises administering to said patient 500 mg mycophenolate mofetil and 5 mg lisinopril.

2. The method according to claim 1, wherein said method treats or lessens the severity of a decline in GFR in said patient.

3. The method according to claim 1, wherein said method decreases proteinuria in said patient.

* * * * *